United States Patent [19]

Barwick et al.

[11] Patent Number: 5,030,199

[45] Date of Patent: Jul. 9, 1991

[54] FEMALE INCONTINENCE CONTROL DEVICE WITH MAGNETICALLY OPERABLE VALVE AND METHOD

[75] Inventors: Carl B. Barwick, Caledonia, Wis.; Rebecca Y. Chin, Mundelein, Ill.

[73] Assignee: Medical Engineering Corporation, Racine, Wis.

[21] Appl. No.: 448,496

[22] Filed: Dec. 11, 1989

[51] Int. Cl.$^5$ ................................................ A61F 2/00
[52] U.S. Cl. ............................ 600/29; 128/DIG. 25; 604/54; 604/63; 604/96
[58] Field of Search ..................... 600/29–30; 604/54, 93, 96–99, 117, 246, 247; 251/65; 128/DIG. 25

[56] References Cited

U.S. PATENT DOCUMENTS

| | | | |
|---|---|---|---|
| 3,503,400 | 3/1970 | Osthagen et al. | 128/DIG. 25 |
| 3,642,004 | 2/1972 | Osthagen et al. | 128/DIG. 25 |
| 3,812,841 | 5/1944 | Isaacson | 600/29 |
| 3,841,304 | 10/1974 | Jones | 600/29 |
| 4,909,788 | 3/1990 | Burton et al. | 604/54 |

FOREIGN PATENT DOCUMENTS

| | | | |
|---|---|---|---|
| 2537506 | 3/1977 | Fed. Rep. of Germany | 128/DIG. 25 |
| 2624418 | 12/1977 | Fed. Rep. of Germany | 128/DIG. 25 |
| 2251302 | 7/1975 | France | 128/DIG. 25 |
| 526357 | 9/1976 | U.S.S.R. | 128/DIG. 25 |

Primary Examiner—Randall L. Green
Assistant Examiner—K. M. Reichle
Attorney, Agent, or Firm—Stuart E. Krieger

[57] ABSTRACT

A female incontinence control device includes a conduit having inlet and outlet openings for receiving, conducting and discharging urinary fluid. The device also includes stabilizing structure, which can be adjustable, for holding the conduit in its installed position relative to the urethra and bladder such that a drainage inlet opening can receive fluid from the bladder, and the outlet discharge opening is positioned outside the urethra. The conduit includes a magnetically actuatable drainage control valve adapted to be positioned between the urethral orifice and the labia majora. Magnetic actuation of the valve from a normally closed position to an open position is thus easily accomplished by manipulating a portable magnet at a distal end of the conduit outside the urethral opening to selectively control urinary flow through the conduit. The method of controlling female incontinence includes the steps of providing and positioning a conduit to receive the urinary fluid and magnetically actuating the valve in the conduit by manipulating a magnet proximal the conduit in the vicinity of the valve to open the valve and allow accumulated urinary fluids to be drained through the outlet opening. Removal of the magnet permits the valve to automatically close.

28 Claims, 5 Drawing Sheets

FEMALE INCONTINENCE CONTROL DEVICE WITH MAGNETICALLY OPERABLE VALVE AND METHOD

BACKGROUND OF THE INVENTION

This invention relates to devices and methods for controlling female incontinence and more particularly to a novel female incontinence control device that employs a magnetically actuatable valve for controlling urinary discharge, and a novel method for controlling urinary discharge.

Urinary incontinence in women is a common condition that can result from a variety of causes including illness, injury or debilitation. An incontinent condition is usually characterized by a weakness or total lack of functioning of the muscles that control expansion and contraction of the urinary sphincter. Thus far there are no known surgical procedures that satisfactorily correct an incontinent condition to the extent that bladder control is substantially restored.

Attempts to ameliorate the condition of incontinence include the use of passive devices such as a collection bag worn by the user to collect urine as it drains from the urethra. One drawback of this arrangement is that the bladder continuously drains into the collection bag without affording the user any control of urinary discharge. A further drawback of this arrangement is that the collection bag must accompany the user and thus inhibits the user's activities. Still another drawback is that the collection bag can provide a path for bacterial infection.

Absorbent pads similar to diapers are another example of a passive remedy for individuals having an incontinent condition. Absorbent pads have disadvantages similar to those described for the collection bag and also require frequent changing.

Other known devices which deal with the problem of female incontinence attempt some form of drainage control and include catheters, draining probes and dilators, such as shown in U.S. Pat. Nos. 4,194,508; 4,198,979 and 4,563,183. Generally such known devices also include an external fluid collection system fastened to a portion of the user's body.

In general, catheters, collection bags and absorbent pads are cumbersome and awkward to use in dealing with incontinence, and are often a source of embarrassment to the user.

Attempts to address such problems as lack of control, bulkiness, discomfort, embarrassment and inhibition of activities have led to the development of valved incontinence control devices, which eliminate the need for external collection systems and allow the user to manually control the flow of urinary fluids from the urinary tract. Examples of such devices are shown in U.S. Pat. Nos. 3,503,400; 3,731,670; 3,939,821 and 4,024,855.

In U.S. Pat .No. 3,503,400, a manually controllable valve is positioned within the urethra near the bladder. The valve is operated by a control cable that passes through the urethra to permit exterior access by the user. Such an arrangement, although permitting positive drainage control, provides a potential path for bacterial infection of the urinary tract, and can also cause discomfort to the user due to the fact that the force on the cable is transferred through the urethra.

In U.S. Pat. No. 3,731,670, a bi-stable magnetic valve member requires a first magnetic actuation from a closed position to an open position and a second magnetic actuation from the closed position back to the open position. Such device, although affording the user some degree of drainage control, is not foolproof. For example, when the valve is subjected to a first actuation into an open position and drainage ceases, a user may forget to administer a second actuation to actuate the valve back into the closed position, or assume that the valve has been actuated into the closed position while it still remains in the open position. Should the valve be left inadvertently in the open position, unexpected drainage will result.

In U.S. Pat. No. 3,939,821 and 4,024,855, magnetic valve members are implanted about the urethra of the user and require external actuating means to cause the valve to operate. Such devices necessitate surgical implantation of the magnetic valve members. Should operational problems occur in these devices, further surgery may be required.

It is thus desirable to provide a female incontinence control device that is magnetically actuatable by the user with a hand-held magnet to control urinary discharge, is relatively easy to use, does not unduly impede normal activity of the user and does not require surgical installation.

OBJECTS AND SUMMARY OF THE INVENTION

Among the several objects of the invention may be noted the provision of a novel female incontinence control device having a magnetically actuatable control valve for controlling urinary discharge, a novel female incontinence control device which is substantially entirely contained within the urethral tract of the user, a novel female incontinence control device which does not require surgical implantation, a novel female incontinence control device which can be operated by manual manipulation of a portable magnet, a novel female incontinence control device which normally prevents urinary discharge to maintain continence and permits such discharge upon simple manipulation of a portable magnet, a novel female incontinence control device which is adjustable for comfortable installation, and a novel method of controlling female incontinence.

Other objects and features of the invention will be in part apparent and in part pointed out hereinafter.

In accordance with the invention, the female incontinence control device includes a conduit having a proximal end with an inlet opening adapted to receive urinary fluids that drain from the bladder, and a distal end with an outlet opening through which urinary fluids are discharged.

A magnetically actuatable discharge control valve provided at the distal end of the conduit is adapted to be located outside the urethral opening. In all embodiments of the invention the distal end portion of the conduit can be supported between the urethral orifice and the labia majora. The control valve is thus accessible for magnetic actuation with a portable, hand held magnet to actuate the control valve into an open condition and selectively control discharge of urinary fluids through the conduit. The accessibility of the control valve for such magnetic actuation does not inhibit general physical activity of the user.

In at least one embodiment of the invention, a valve member of the control valve is projectable from the distal end portion of the conduit when the control valve is magnetically actuated into an open condition. A sealing diaphragm is provided across the projectable portion of the valve member to take up any movement of the valve member as it projects from the distal end portion of the conduit.

In some embodiments of the invention, the magnetically actuatable portion of the valve is entirely confined within the distal end portion of the conduit when the valve is actuated into an open condition.

Other embodiments of the invention provide for location of the valve in a central axial portion of the conduit, or at an offset angular portion of the conduit, or in a projecting structure of the conduit at a distal end portion thereof.

The conduit also includes holding means for stabilizing the installed position of the conduit in the urethra. The holding means include a bladder engaging structure at the proximal end portion and an anchoring structure at the distal end portion. The anchoring structure is of a size and shape that permits disposition between the meatus and the labia majora. In a further embodiment of the invention, the anchoring structure is adjustable to a desired distance from the bladder engaging structure to correspond to the length of the urethral tract.

All embodiments of the invention can include a lumen for infusing antimicrobial agent into the urethra to avoid bacterial infection.

In using the female incontinence control device the conduit is positioned in the urethra such that the outlet opening of the conduit and the control valve which controls discharge of urinary fluid through the outlet opening are accessible outside of the urethral opening.

The magnetically actuatable control valve has a normally closed position and thus will normally allow urinary fluid to accumulate without any intervention by the user. When the user so desires, she can actuate the control valve into an open condition by magnetic actuation of the magnetically actuatable member. Such actuation is accomplished by manipulating a portable magnet at the distal end portion of the conduit, as by holding the magnet at the distal end to attract the magnetically actuatable member or slightly moving the magnet to cause corresponding movement of the magnetically actuatable member within the valve.

When the user holds the portable magnet at the distal end portion of the valve, the valve is maintained in an open condition to permit discharge of urinary fluid. When discharge is completed, removal of the actuating magnet from the distal end portion of the conduit enables biasing means within the valve to automatically move the valve to its normally closed position. As a safety factor the biasing means can be selected to permit the valve to open at a predetermined pressure level that avoids the possibility of injury to the bladder or kidneys because of excessive pressure buildup in the bladder.

The user, under normal circumstances, is thus capable of maintaining continence in a passive manner and obtaining urinary discharge through use of the actuating magnet whenever such discharge is desired.

The invention accordingly comprises the constructions and method hereinafter described, the scope of the invention being indicated in the claims.

DESCRIPTION OF THE DRAWINGS

In the accompanying drawings.

Corresponding reference character indicate corresponding parts throughout the several views of the drawings.

DETAILED DESCRIPTION OF THE INVENTION

A female incontinence control device incorporating one embodiment of the invention is generally indicated by the reference number 10 in FIGS. 1-4.

The device 10 includes a conduit 12 having an inlet opening 14 at a proximal end portion 16 and an outlet opening 18 at a distal end portion 20. The conduit 12 also includes a diametrical enlargement 21 at the distal end portion 20. The inlet and outlet openings 14 and 18 communicate through a lumen 22 formed within the conduit 12. The lumen 22 constitutes a drainage passage for urine from the bladder 24 of a user to the outlet opening 18 of the conduit 12.

To maintain stability of the conduit 12 in its installed position in the urethra 26 and to prevent migration of the conduit 12 relative to the urethra 26, anchoring structures larger than the diameter of the urethra are provided at the proximal and distal end portions 16 and 20 of the conduit 12. For example, a bladder engaging member such as a conventional inflatable bladder balloon 28 is provided on the conduit 12 distally of the inlet opening 14 for location at a neck portion 30 of the bladder 24. In addition, an oval or egg-shaped flange 32 is provided at the diametrical enlargement 21 of the conduit 12 at the distal end portion 20. The flange 32 is adapted to be positioned outside the urethral orifice 36 to bear against the meatus 37. The flange 32 is sized and shaped to prevent retrograde movement of the flange into the urethral passage 26 toward the bladder 24. If desired, the flange 32 can be formed in other suitable shapes that will prevent such retrograde movement.

The bladder balloon 28 is inflated through a lumen 38 having a proximal end 40 that opens into the interior of the balloon 28. The inflation lumen 38 does not communicate with the drainage lumen 22.

An inflation check valve, generally indicated at 42 is provided at the diametrical enlargement 21 at a distal end 44 of the inflation lumen 38 and is accessed through a passage 46 at the distal end 44. Inflation fluid (not shown) is thus introduced into the bladder balloon 28 through the check valve 42 by inserting a known inflation device such as an inflation syringe (not shown) into the passage 46. The inflation syringe infuses fluid past a spring biased ball check 48 to inflate the bladder balloon 28.

Although the anchoring structure of the device 10 is represented by the inflatable bladder balloon 28 and the flange 32, it will be apparent to those skilled in the art that other suitable known anchoring structures can be employed, such as, for example, non-inflatable collapsible bulges, Malecot tips and spirals.

Figures 2, 3, 4:
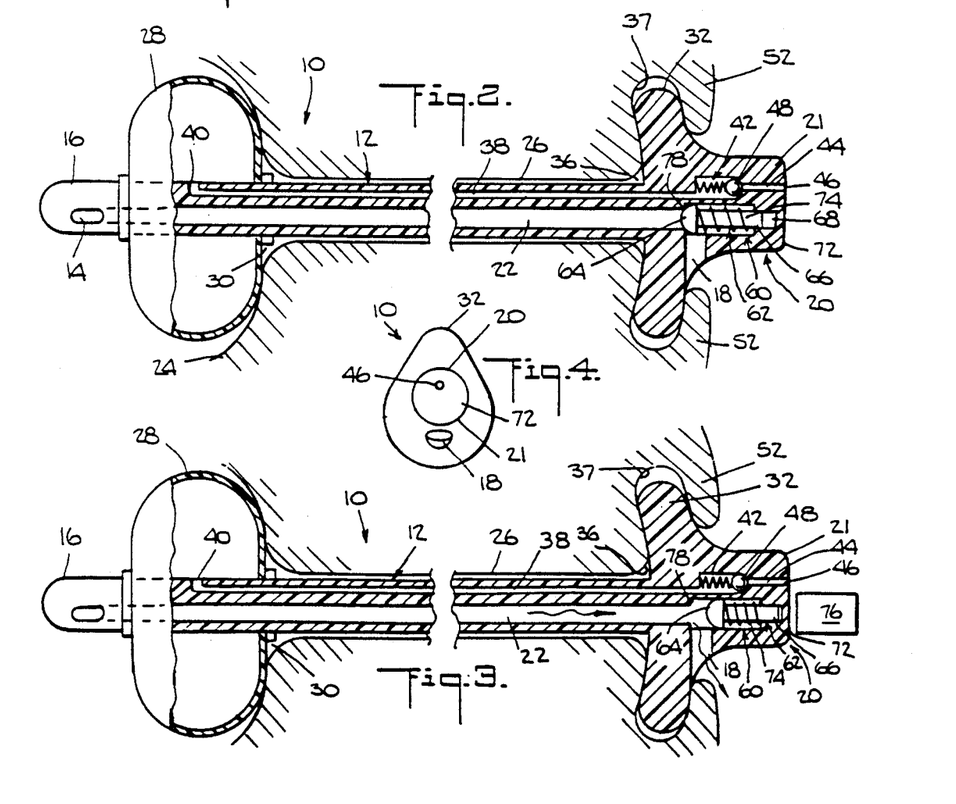
FIG. 2 is an enlarged view thereof partly shown in section, of the valve means therein, in a normally closed position.
FIG. 3 is a view similar to FIG. 2 showing the valve means in an open position.
FIG. 4 is a distal end view thereof.

Referring to FIGS. 2 and 3, a magnetically actuatable valve generally indicated at 60 is provided at the distal end portion 20 of the conduit 12 in the enlarged diametrical portion 21.

The valve 60 includes a valve member 62 having a generally hemispherical valve head 64 joined to a valve stem 66. The valve head 64 can be formed of a suitable elastomeric material such as silicone and the valve stem 66 can be formed of a suitable magnetically attractive or magnetized material such as neodymium-iron-boron or samarium cobalt.

The valve member 62 is slidably movable in a valve passage 68 and is biased by a biasing spring 74 to a normally closed position wherein the valve head 64 engages a valve seat 78.

When the valve member 62 is in its normally closed position as shown in FIG. 2, the valve stem 66 is spaced a predetermined amount from an end surface 72 of the enlarged diametrical portion 21.

Figure 1:
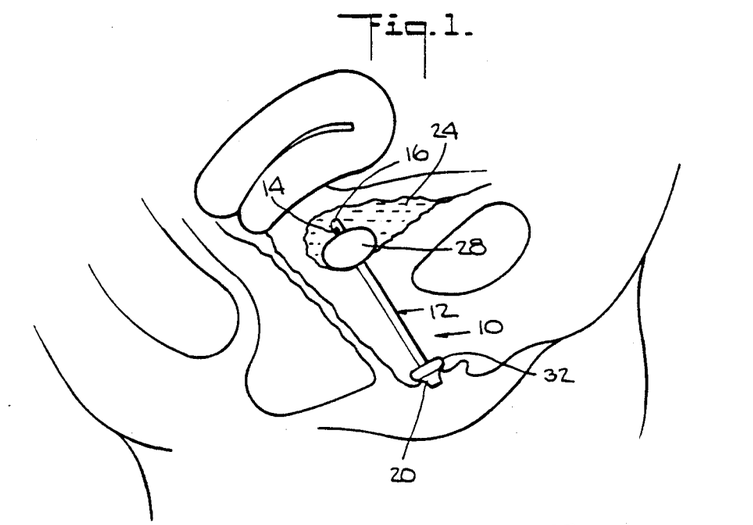
FIG. 1 is a simplified schematic anatomical view showing the general location of an incontinence control device incorporating one embodiment of the invention.

The incontinence control device 10 is inserted into the urethra 26 in a conventional manner similar to that in which a Foley catheter is inserted. After insertion of the device 10, a suitable known syringe or inflation connector (not shown) may be used to inject inflation fluid directly into the inflation lumen 38, via the access passage 46 and valve 42 to inflate the bladder balloon 28.

The device 10 is thus installed as shown schematically in FIG. 1. With the valve 60 in a normally closed position as shown in FIG. 2, urine cannot drain through the drainage lumen 22 and therefore accumulates in the bladder 24. The normally closed position of the valve 60 maintains continence for the user.

When bladder discharge is desired, the user manipulates a portable activating magnet 76 to the end surface 72 of the conduit 12. The magnet 76 can be formed of neodymium-iron-boron and polysulfone. The magnet 76 overcomes the biasing force of the biasing spring 74 and attracts the valve member 62 away from the valve seat 78 as shown in FIG. 3 to place the valve 60 in an open condition. Attraction of the valve member 62 by the magnet 76 causes the valve stem 66 to move toward the end surface 72. The valve member 62 will remain in its magnetically attracted position corresponding to the open condition of the valve 60 as long as the actuating magnet 76 is held next to the valve member 62.

With the valve 60 in the open condition fluid can flow from the bladder through the drainage lumen 22 for discharge from the outlet opening 18. The bladder discharge can be easily and conveniently directed into a toilet in the same manner that such discharge is accomplished by individuals who do not require an incontinence device.

After bladder discharge is completed the user removes the magnet 76 from the end surface 72 of the conduit 12, allowing the valve member 62 to return to its normally closed position under the influence of the biasing spring 74.

The device 10 thus restores continence and affords the user complete control of bladder discharge without impediment and without the need for external collection devices or actuating structures that extend from the body.

The magnet 76 can be placed in a pocket, a pocketbook or can be formed in a decorative shape to be worn on a necklace or bracelet for convenient access. Other options include forming the magnet for retention in a keycase or on a keychain, or as part of a ring.

Figures 18, 19, 20:
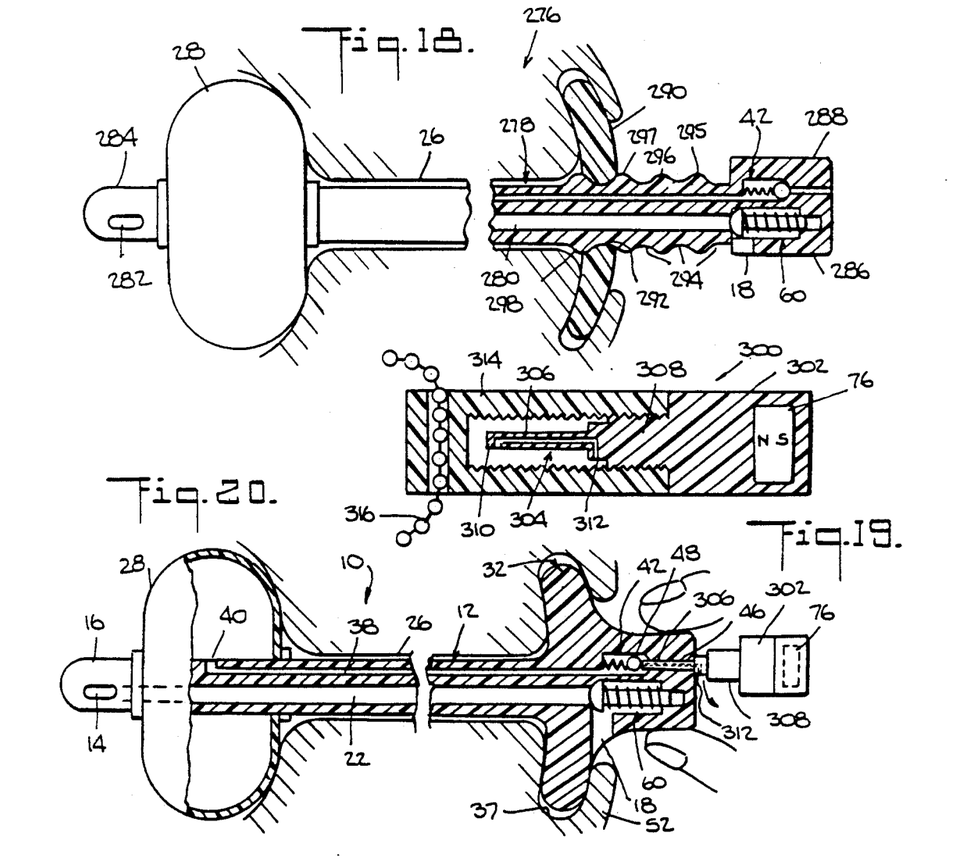
FIG. 19 is a sectional view of a magnet holder and deflator needle for the incontinence control device.
FIG. 20 is a simplified schematic view, partly shown in section, of the embodiment of FIG. 1 undergoing deflation.

For example, referring to FIG. 19, a portable magnet holder 300 includes a housing 302 containing the magnet 76. If desired, the housing 302 can also include a deflator device 304 including a deflator needle 306 projecting from a threaded neck portion 308. The needle 306 includes an inlet opening 310 and an outlet opening 312. The threaded neck portion 308 is threaded to a hollow holder member 314 that is provided with a key chain or necklace 316.

Referring to FIG. 20, the deflator needle 304 is sized to fit into the inflation valve access passage 46 at the enlarged diametrical portion 21. When deflation of the bladder balloon 28 is needed, the deflator device 304 is unthreaded from the holder member 314 and the deflation needle 306 is urged against the ball check 48 of the inflation valve 42 to open the valve 42. Fluid is thus permitted to drain from the bladder balloon 28 through the inflation lumen 38, past the inflation valve 42 into the opening 310 of the deflator needle 306 for discharge through the outlet opening 312.

The magnet holder 300 is preferably cylindrical in shape having an overall length of approximately 2 inches and a diameter of approximately 0.6 inches. If the deflator device 304 is omitted from the magnet holder 300, the overall length of the magnet holder device can be reduced in size to less than an inch.

As another alternative for removing the device 10 from the urethra 26, should such removal be desired, the distal end 20 of the conduit 12 at the diametrical enlargement 21 can be cut with a suitable device such as a scissor at a point upstream of the inflation valve 42. The inflation lumen 38 can thus be bled to accomplish deflation of the bladder balloon 28. Once the bladder balloon 28 is deflated, the conduit 12 can be easily withdrawn from the urethra 26 and discarded.

If desired, the device 10 can be incorporated with a closed inflation system (not shown), wherein the bladder balloon 28 communicates with an inflation reservoir balloon (not shown). The reservoir balloon is connected to the inflation passage 38 for communication with the check valve 42. The inflation reservoir eliminates the need for a syringe or inflation connector. Pressure on the reservoir balloon after installing the device 10 in the urethra 26 causes the check valve 42 in the inflation lumen 38 to open, allowing the bladder balloon 28 to inflate. The inflation reservoir can be removed after installation of the device 10 is completed. In this variation of the device 10, removal is also accomplished in the same manner as previously described, as by using the deflation device 304, or a scissor upstream of the check valve 42 to cut through the inflation lumen 38.

Figure 5:
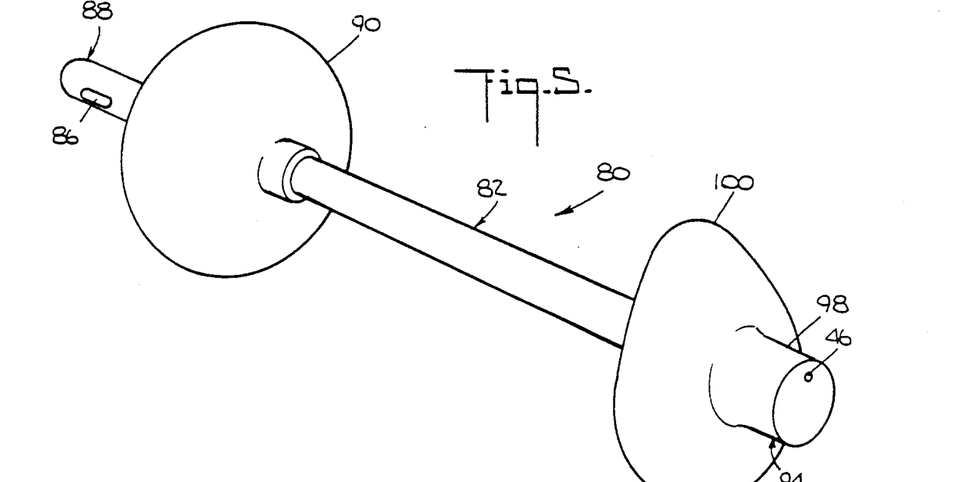
FIG. 5 is a simplified perspective view of another embodiment of the invention.
Figure 6:
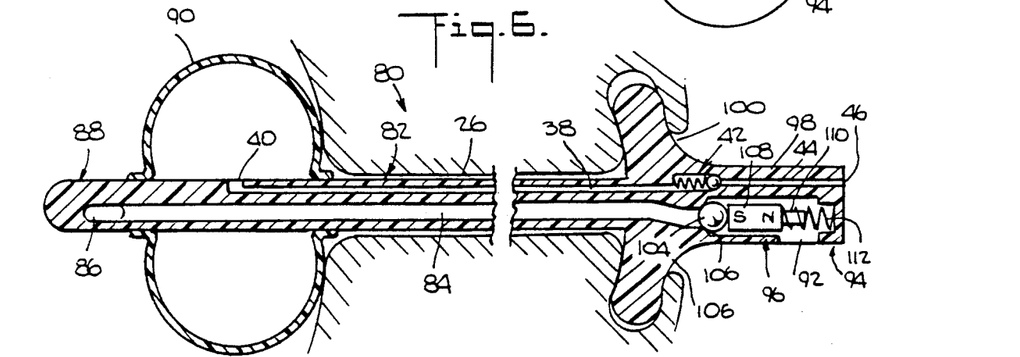
FIG. 6 is a simplified sectional view thereof with the valve means in a normally closed position.
Figure 7:
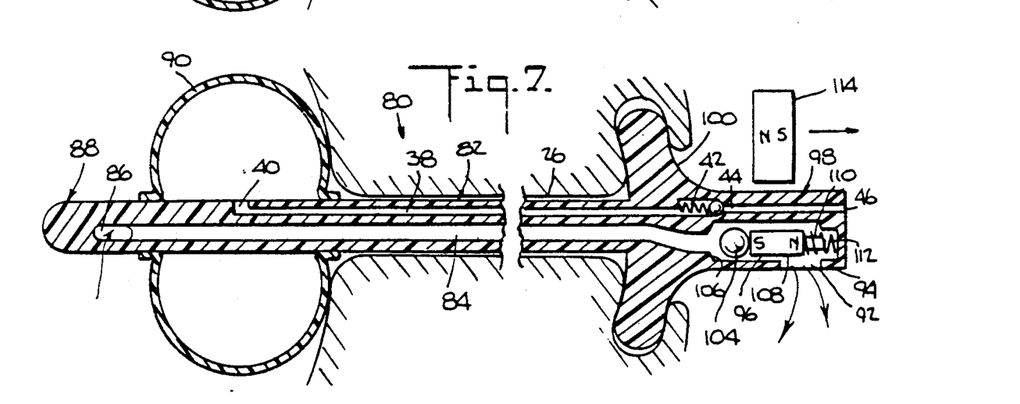
FIG. 7 is a view similar to FIG. 6 with the valve means in an open position.

Another embodiment of the female incontinence control device is generally indicated by the reference number 80 in FIGS. 5-7. The device 80 includes a conduit 82 having a drainage lumen 84. The drainage lumen 84 includes an inlet opening 86 at a proximal end 88 of the conduit 82 that communicates with a bladder balloon 90, and an outlet opening 92 at a distal end 94 of the conduit 82. A magnetically actuatable valve 96 at the distal end 94 controls discharge of fluid through the outlet opening 92.

The distal end 94 of the conduit 82 also includes an enlarged diametrical portion 98 with a flange 100 similar in shape to the flange 32 of the device 10.

The valve 96 includes a ball check 104, which is held in a normally closed position against a valve seat 106 by a magnetic member 108 having a stem portion 110. The ball check 104 can be formed of silicone or any other suitable elastomeric material. The magnetic member 108 is normally biased against the ball check 104 by a biasing spring 112 to maintain the ball check 104 in a normally closed position as shown in FIG. 6.

The device 80 is installed in the urethra 26 in a manner similar to that described for the device 10. Operation of the device 80 is accomplished by placing a magnet 114, which is similar to the magnet 76, at the enlarged diametrical portion 98 of the conduit 82. The magnet 114 is manipulated to attract the magnetic member 108 away from the valve seat 106. Movement of the magnetic member 108 away from the valve seat 106 releases the ball check 104 from the valve seat 106 and places the valve 96 in an open condition as shown in FIG. 7. The valve 96 remains in the open condition as long as the magnet 114 is present at the enlarged diametrical portion 98. The presence of the magnet 114 thus overcomes the biasing force of the biasing spring 112.

With the valve 96 in an open condition, bladder fluid can flow through the drainage lumen 84 and past the valve seat 106 for discharge through the outlet opening 92 of the conduit 82. When discharge is completed the valve 96 is automatically movable to the closed position of FIG. 6 upon removal of the magnet 114 from the enlarged diametrical portion 98. Removal of the magnet 114 enables the biasing spring 112 to urge the magnetic member 106 and the ball check 104 into the valve closed position wherein the ball check 104 is seated against the valve seat 106.

Figures 8, 9, 10, 11:
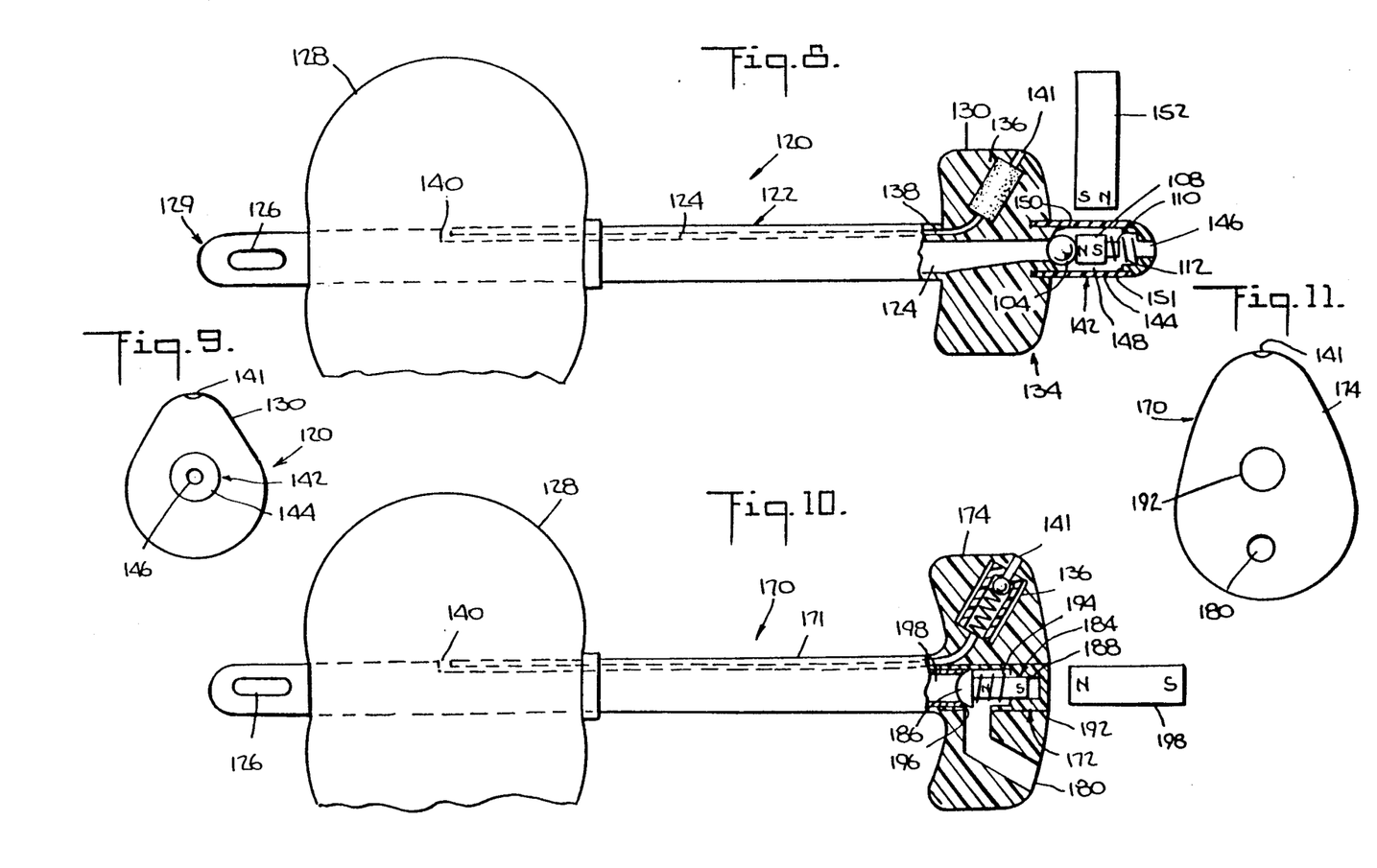
FIG. 8 is an enlarged simplified schematic view partly shown in section, of another embodiment of the invention, wherein the valve means is in a normally closed position.
FIG. 9 is a distal end view thereof.
FIG. 10 is an enlarged simplified schematic view partly shown in section, of still another embodiment of the invention, wherein the valve means is in a normally closed position.
FIG. 11 is a distal end view thereof.

Still another embodiment of the female incontinence control device is generally indicated by the reference number 120 in FIGS. 8 and 9. The incontinence control device 120 includes a conduit 122 having a drainage lumen 124 with an inlet opening 126 and a bladder balloon 128 at a proximal end portion 129. A flange 130 similar in shape to the flange 32 is provided at a distal end portion 134 of the conduit 122.

An inflation check valve 136 similar to the inflation check valve 42 is formed in the flange 130 at a distal end of an inflation lumen 138 that opens at 140 into the chamber of the bladder balloon 128. The inflation check valve 136 is accessible by any known inflation device through an access passage 141.

The distal end portion 134 of the conduit 122 includes a drainage control valve 142 having a valve shell 144 joined to the flanges 130 and 132 in any suitable known manner as, for example, by bonding. The valve shell 144 can be formed of silicone. If desired, the valve shell 144 can be formed as an integral extension of the distal end portion 134 as in the devices 10 and 80.

The valve shell 144 includes a discharge opening 146 and a valve chamber 148 which accommodates a spherical ball check 104, a magnetic member 108 and a biasing spring 112. The biasing spring 112 is arranged around a stem 110 of the magnetic member 108 to urge the magnetic member 108 against the ball check 104 thus normally seating the ball check 104 in a valve seat 150 formed at the distal end 134 of the conduit 122. The discharge opening 146 and the valve chamber 148 are continuations of the drainage lumen 124.

The incontinence device 120 is installed and used in a manner similar to that previously described for the device 10. The valve 142 is maintained in a normally closed position by the force of the biasing spring 112 against the magnetic member 108 which, in turn, maintains the ball check 104 against the valve seat 150. In this manner the bladder (not shown) is permitted to accumulate fluid.

When discharge of bladder fluid is desired, a magnet 152, similar to the magnet 76, is manipulated to the distal end 134 of the conduit 122 at the valve shell 144. The magnet 152 attracts the magnetic member 108 toward the discharge opening 146 thereby releasing the ball check 104 from the valve seat 150. The magnetic force applied by the magnet 152 is sufficient to overcome the resistance of the biasing spring 112 to permit release of the ball check 104 from the valve seat 150. Movement of the magnetic member 108 toward the discharge opening 146 is limited by an annular step 151 formed in the valve shell 144.

Accumulated fluid in the bladder can thus flow through the drainage lumen 124 past the valve seat 150 for discharge through the discharge opening 146 of the valve housing 142. When discharge is completed, the magnet 152 is manipulated away from the valve shell 144 to enable the biasing spring 152 to once again urge the magnetic member 108 against the ball check 104 to force the ball check 104 against the valve seat 150. The valve 142 is thus automatically returned to its normally closed position to prevent bladder discharge.

A further embodiment of the female incontinence control device is generally indicated by the reference number 170 in FIGS. 10 and 11.

The device 170, which includes a conduit 171, differs from the device 120 by provision of a magnetically actuatable valve 172 that does not have a projecting valve shell. The valve 172 is recessed within the anchoring flange 174 of the conduit 171. The flange 174 is similar in shape to the flange 32 of the device 10. A discharge outlet opening 180 is also formed in the flange 174.

The valve 172 includes a valve member 184 having a hemispherical head portion 186 similar to the hemispherical head portion 64 of the valve 60. The valve member 184 also includes a magnetic valve stem 188 similar to the valve stem 66 of the valve 60.

A biasing spring 194, similar to the spring 112, is provided around the valve stem 188 to urge the valve member 184 into a normally closed position wherein the head portion 186 is seated against a valve seat 196 formed at an intermediate portion of a fluid drainage passage 198 in the conduit 171. The discharge opening 180 is a continuation of the drainage passage 198. The device 170 is otherwise structurally similar to the device 120.

The device 170 is installed and operated in a manner similar to that previously described for the device 10. To permit urinary discharge, a portable magnet 198 similar to the magnet 152, is manipulated at the opening 190 to attract the valve member 184 away from the valve seat 196 thereby positioning the valve 172 in an open condition. With the valve 172 in an open condition, the valve stem 188 is shifted toward a distal end surface 192 of the flange 174 and fluid flows through the drainage passage 198 for discharge at the discharge opening 180.

Figures 12, 13, 14, 15, 16:
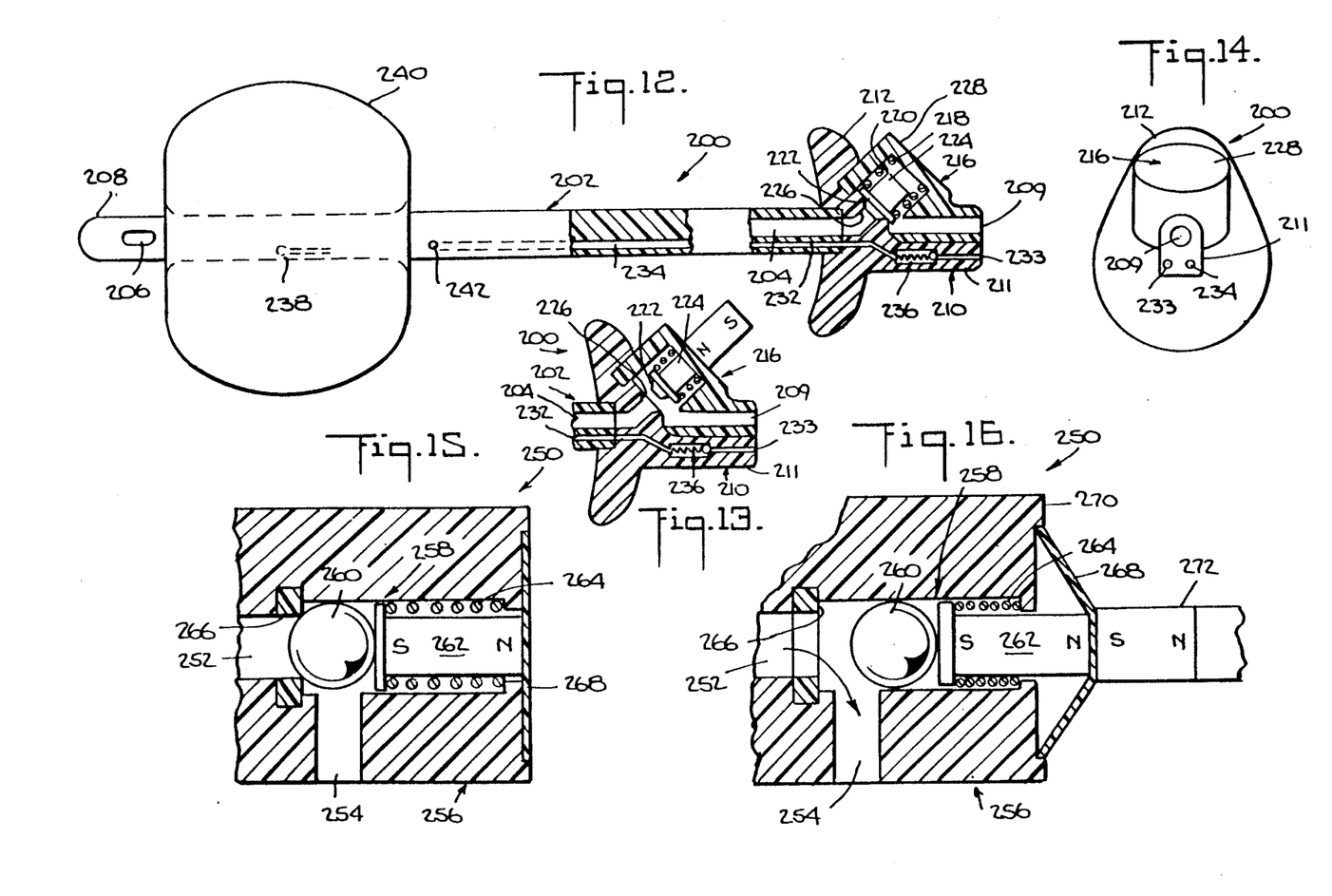
FIG. 12 is an enlarged simplified schematic view partly shown in section, of a further embodiment of the invention, wherein the valve means is in a normally closed position.
FIG. 13 is a fragmentary detail thereof showing the valve means in an open position.
FIG. 14 is a distal end view thereof.
FIG. 15 is a still further embodiment of the invention wherein the valve means is shown in a normally closed position.
FIG. 16 is a view similar to FIG. 15 wherein the valve means is shown in an open condition.

A further embodiment of the female incontinence control device is generally indicated by the reference number 200 in FIGS. 12–14.

The device 200 includes a conduit 202 having a drainage lumen 204 with an inlet opening 206 at a proximal end 208 and an outlet opening 209 at a distal end portion 210. The distal end portion 210 of the conduit 202 includes an enlarged distal section 211 and a flange 212 similar in shape to the flange 32.

A valve 216 is provided at the distal end portion 210 between the enlarged distal section 211 and the flange 212. The valve 216 includes a valve member 220 having a poppet head 222, and a stem portion 224 formed of a suitable magnetic material of the type previously disclosed. The valve 216 further includes a biasing spring 218 that normally biases the poppet head 222 against a valve seat 226. The valve 216 also includes an exterior inclined end surface 228.

The device 200 further includes an inflation lumen 232 for inflating a bladder balloon 240 and a lumen 234 for introducing a suitable known antimicrobial agent into the urethra (not shown). The inflation lumen 232 is accessible through an access passage 233 at an end surface 235 of the enlarged section 211 through a check valve generally indicated by the reference number 236. The inflation lumen 232 includes an outlet end 238 that communicates with the interior of the bladder balloon 240. The antimicrobial infusion lumen 234 is also accessible at the end surface 235 of the enlarged section 211 and includes a proximal open end 242 in the wall of the conduit 202. The opening 242 is at a predetermined distance from the flange 212 to ensure that such opening is at a proximal end portion of the urethra.

The device 200 is installed in a manner similar to that previously described for the device 10. Operation of the device 200 is also similar to that previously described for the device 10. Thus a portable magnetic actuating member (not shown) is manipulated against the end surface 228 of the valve 216 to actuate the valve member 220 into an open position by magnetically attracting the valve stem 224 toward the end surface 228. (See FIG. 13) With the valve member 220 in an open condition fluid can drain from the bladder through the drainage lumen 204 past the valve seat 226 for discharge through the outlet opening 209. Removal of the magnet permits the valve 216 to automatically close.

The lumen 234 for infusion of an antimicrobial agent is accessed in the same manner as the inflation lumen 232 and is used for flushing an antimicrobial agent into the urethra to guard against infection of the urethra.

It will be noted that since the valve 216 is offset from the longitudinal axis of the conduit 202 and spaced from the discharge opening 209, the enlarged distal section 211 can be of a relatively smaller size than the enlarged diametrical sections 21 and 98 of the devices 10 and 120.

In a further embodiment of the invention which is a variation of the device 200, the lumen 234 for infusing antimicrobial material is omitted from the device 200. The further embodiment is otherwise identical to the device 200.

A still further embodiment of a female incontinence control device is generally indicated by the reference number 250 in FIGS. 15 and 16. The proximal end portion structure (not shown) and the structure intermediate the proximal and distal end portions (not shown) of the device 250 includes a conduit, bladder balloon and infusion lumen similar to the structure of the previously described embodiments, and are omitted herein for purposes of simplicity.

The device 250 includes a fluid drainage passage 252 having an outlet opening 254 at a distal end portion 256. The distal end portion 256 is provided with a control valve 258 at a location similar to the location of the valve 60 of the device 10. The valve 258 comprises a spherical ball check 260, a magnetic member 262 and a biasing spring 264 arranged to urge the magnetic member 262 against the ball check 260 to maintain the ball check 260 in a normally closed position against a valve seat 266.

The valve 258 further includes a resilient diaphragm seal 268 at an end surface 270. The diaphragm seal 268 can be formed of a suitable biocompatible material such as silicone.

The device 250 is installed in a manner similar to that previously described for the device 10. The valve 258 of the device 250 is in a normally closed position thereby preventing fluid drainage. When fluid discharge is desired, the valve 258 is magnetically actuated with a portable magnet 272 (FIG. 15) into a valve open condition. Such actuation is accomplished by manipulating the portable magnet 272 adjacent the diaphragm 268 to attract the magnetic member 262 away from the valve seat 266 thereby releasing the ball check 260 from the valve seat 258. Fluid is thus permitted to drain through the drainage lumen 252 past the valve seat 266 for discharge from the opening 254. Removal of the magnetic member 272 from proximity of the diaphragm 264 permits the valve 258 to resume its normally closed position to maintain the continence of the user.

It should be noted that all of the devices described herein can include a lumen for infusing an antimicrobial agent into the urethra of the type previously described for the device 200. In addition, the biasing springs of each device can have a predetermined restraint that is overcome at a pressure level that obviates the possibility of pressure damage to the urethra or bladder if a magnetic actuating member is not available.

Figure 17:
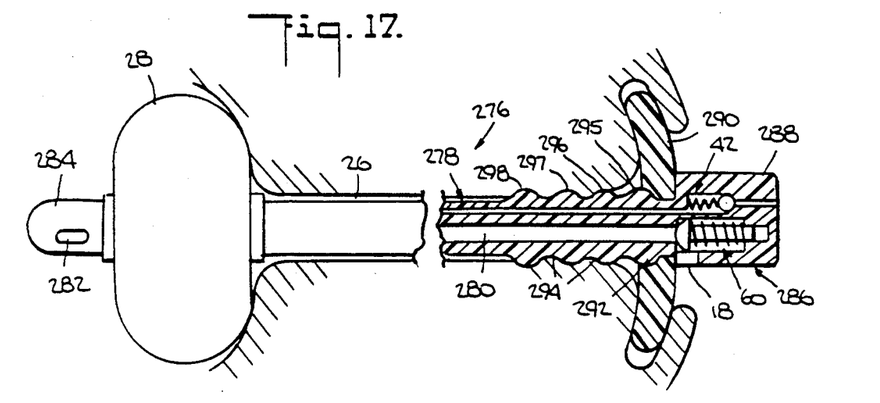
FIGS. 17 and 18 are enlarged, simplified, schematic views, partly shown in section, of yet another embodiment of the invention.

Another embodiment of the female incontinence control device is generally indicated by the reference number 276 in FIGS. 17 and 18. The device 276 includes a conduit 278 having a drainage lumen 280 with an inlet opening 282 at a proximal end portion 284.

A magnetically actuatable valve 60 is provided in an enlarged diametrical portion 286 at a distal end portion 288 of the conduit 278 and controls discharge of fluid through the drainage lumen 280. The distal end portion 288 also includes an adjustable egg-shaped ring-like flange 290, preferably formed of a soft elastomeric material such as silicone, similar in shape to the flange 32. A circular opening 292 in the flange 290 is sized for disposition in a selected depression 294 provided between circumferential ribs such as 295, 296, 297 and 298 formed on the conduit 278 near the enlarged diametrical portion 286. The device 276 is otherwise structurally similar to the device 10 including a bladder balloon 28 provided near the proximal end portion 284 inflatable through an inflation lumen 38. An inflation control valve 42 controls admission of inflation fluid into the bladder balloon 28.

The flange 290 is preferably relatively flexible in comparison to the conduit 278 to facilitate axial positioning of the flange 290 along the conduit 278 at the circumferential ribs 295, 296, 297 and 298. The flange 290 can thus be selectively positioned between any two adjacent circumferential ribs 295, 296, 297 and 298 to change the position of the flange 290 relative to the bladder balloon 28. Under this arrangement, a selected length of the conduit 278 can be positioned between the bladder balloon 28 and the flange 290 to correspond with the length of the urethra 26. Installation and operation of the device 276 is accomplished in a manner similar to that previously described for the device 10.

It should be noted that the spacing between the enlarged diametrical portion 286 and the flange 290 in FIG. 18 is exaggerated for purposes of clarity. In actual use, the enlarged diametrical section would not unduly project beyond the labia majora. Thus in any adjustment situation, the maximum and minimum adjustment range would be selected so as to assure functional and convenient operation by the user.

Some advantages of the present invention evident from the foregoing description include a magnetically actuatable female incontinence control device that is operable by a user through simple manipulation of a portable hand held magnet. The incontinence control device does not require any external collection system and does not require surgical implantation or electromagnetic actuation. The novel arrangement of the control valve at a distal end portion of the drainage conduit permits easy access to the valve for magnetic actuation by a user. Anchoring means which can be adjustable to stabilize the control device at the urethral opening and can be conveniently located intermediate the labian fold and the meatus. Thus the user is relatively free of impediment in carrying out normal activities as compared to known devices that require the use of external collection systems or components that extend away from the labia. A further advantage of the present device is the facility of the user in obtaining urinary discharge whenever it is convenient to do so and to maintain continence at other times.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. An incontinence device for a female, comprising conduit means for receiving, conducting, and discharging urinary fluids from the bladder, said conduit means including a conduit member having opposing inlet and outlet openings, means for holding said conduit member in a predetermined position relative to the urethra such that said inlet opening is received in the bladder and said outlet opening is positioned outside the urethra, and magnetically actuatable valve means having a normally closed position, said valve means being positioned within said conduit means proximate the outlet opening such that said valve means is positioned outside the urethra for magnetic actuation from outside said urethra from said closed position to an open position for selectively controlling the flow of urinary fluid through said conduit means for discharge through said outlet opening.

2. The incontinence device as claimed in claim 1 wherein said valve means includes a magnetically actuatable member normally positioned to maintain said valve means in said closed position.

3. The incontinence device as claimed in claim 1 wherein said valve means includes a valve member normally maintained in said closed position, said valve member being releasable from said closed position by magnetic actuation of said valve means to permit movement of said valve member from said closed position to said open condition to permit flow of urinary fluid through said conduit means for discharge through said outlet opening.

4. The incontinence device as claimed in claim 3 wherein said valve means further includes means for urging said valve member in said normally closed position.

5. The incontinence device as claimed in claim 3 wherein said valve means further includes a magnetically actuatable member engagable with said valve member to maintain said valve member in said closed position, said valve member being releasable from said closed position upon magnetic actuation of said magnetically actuatable member away from said valve member.

6. The incontinence device as claimed in claim 5 wherein said magnetically actuatable member is spring biased against said valve member.

7. The incontinence device as claimed in claim 1 wherein said valve means includes a valve member normally maintained in said closed position, said valve member being movable to said open condition by magnetic actuation of said valve means to permit flow of urinary fluid through said conduit means for discharge through said outlet opening.

8. The incontinence device as claimed in claim 7 wherein said valve member is formed of magnetically actuatable material and is movable from said closed position to said open position by magnetic actuation of said magnetically actuatable material.

9. The incontinence device as claimed in claim 7 wherein said valve means further includes means for urging said valve member in said normally closed position.

10. The incontinence device as claimed in claim 8 wherein said valve means comprises a valve member having a displaceable sealing surface, said valve member being axially movable within said conduit means, between a valve member open condition upon actuation of said valve means and a valve member normally closed position.

11. The incontinence device as claimed in claim 10 wherein said displaceable sealing surface is formed as part of a sphere.

12. The incontinence device as claimed in claim 10 wherein said displaceable sealing surface is formed as part of a hemisphere.

13. The incontinence device as claimed in claim 10 wherein said displaceable sealing surface is formed as part of a poppet valve member.

14. The incontinence device as claimed in claim 1 wherein said valve means includes a magnetically actuatable member, a valve chamber for accommodating displacement of said magnetically actuatable member and a resilient diaphragm for sealing a portion of said valve chamber, and wherein magnetic actuation of said magnetically actuatable member places said valve means in said open condition and causes movement of said magnetically actuatable member toward said resilient diaphragm to deflect said resilient diaphragm to take up a predetermined movement of said magnetically actuatable member.

15. The incontinence device as claimed in claim 1 wherein said holding means include means for preventing migration of said valve means into the urethra, said migration preventing means permitting positioning of said outlet opening outside the urethral orifice.

16. An incontinence device according to claim 15 wherein said migration preventing means includes a flange member projecting from said conduit member, said flange member being of predetermined size for self containment within the labia majora.

17. An incontinence device according to claim 1 wherein said conduit means includes a distal end portion containing said outlet opening and said valve means and wherein said holding means includes means provided on said distal end portion for preventing migration of said valve means into the urethra.

18. An incontinence device according to claim 17 wherein said means for preventing migration comprises a flange-like member on said conduit member contoured to fit between the urethral meatus and the labia majora to permit positioning of said outlet opening outside the urethral orifice.

19. An incontinence device according to claim 17 wherein said conduit member has a proximal end portion containing the inlet opening, said conduit member having a predetermined longitudinal extent to extend through the urethra to position the outlet opening outside said urethra, and wherein said holding means include a bladder engaging member carried by the proximal end portion to prevent withdrawal of the conduit means from the urethra.

20. An incontinence device according to claim 19 wherein said migration preventing means comprises flange means at the distal end portion of said conduit means.

21. An incontinence device according to claim 20 wherein said conduit member includes a lumen having an inlet opening at the distal end portion of said conduit and an outlet opening a predetermined distance from said flange means to communicate with said urethra to permit infusion of an antimicrobial agent through said lumen into said urethra.

22. An incontinence device according to claim 19 wherein said migration preventing means includes a flange member at the distal end portion of said conduit means, and means for adjusting the distance between said flange member and said bladder engaging member.

23. An incontinence device according to claim 22 wherein said adjusting means comprises a plurality of axially spaced, circumferential ribs and depressions formed on said conduit member, and said flange member is a deformable annular flexible member having an internal diameter greater than the external diameter of said conduit member at said depressions but less than the external diameter of said conduit member at said ribs, to permit selective axial positioning of said flange member on said conduit member at a selected depression to provide for adjustability of the length of the conduit that is positioned between the bladder engaging member and the flange member to correlate with the length of the urethra.

24. An incontinence device comprising a conduit having a proximal end portion with an inlet opening for receipt in the bladder, a distal end portion with an outlet opening for discharging urinary fluid, and a passageway intermediate said inlet and outlet opening for conducting said urinary fluid from said inlet opening to said outlet opening, means for holding said conduit in a predetermined position relative to the urethra, said holding means including a positioning member provided at said distal end portion of said conduit for disposition between the urethral orifice and the labia majora, said positioning member having a predetermined cross sectional magnitude greater than the magnitude of the urethral orifice to prevent proximal migration of said conduit, valve means provided at said distal end portion for controlling the discharge of urinary fluid through said outlet opening, said valve means being magnetically actuatable at said distal end portion from a closed position to an open condition to selectively control discharge of urinary fluid from said outlet opening.

25. The incontinence device according to claim 24 wherein said valve means includes a magnetic member actuatable with a portable manually manipulable magnet to move said valve means from said closed position to said open condition.

26. An incontinence device according to claim 24 wherein said conduit means includes a bladder engaging member at said proximal end portion and a lumen having a lumen inlet opening extending from the distal end portion of said conduit and a lumen outlet opening intermediate said bladder engaging member and said positioning member to permit infusion of an antimicrobial agent through said lumen to flush the urethral passage with said antimicrobial agent.

27. A method of controlling female incontinence comprising providing a conduit predeterminedly dimensioned to be partly positionable in the female urethra, said conduit having opposing inlet and outlet openings with a connecting passageway therebetween and a magnetically actuatable control valve for controlling flow of urine through the passageway past the outlet opening, positioning the outlet opening and the control valve proximal the labia majora of a female, positioning the inlet opening of the conduit to receive substantially all of the urinary fluids which drain from the bladder, so that the control valve, when closed, permits accumulation of urinary fluids, when open, allows the urinary fluids to pass through the conduit for discharge from the outlet opening, and selectively opening the control valve by manipulating a portable magnet at the control valve to magnetically actuate the valve into an open condition and allow the accumulated urinary fluids to discharge through the outlet opening.

28. The method of claim 27, wherein the step of manipulating a magnet includes holding a magnet proximal the labia majora adjacent the conduit in the vicinity of the control valve to cause the valve to open and removing the magnet from proximity to the labia majora to enable the control valve to automatically close when magnetic actuation is removed.

* * * * *